United States Patent
Ellsworth et al.

(10) Patent No.: US 8,895,667 B2
(45) Date of Patent: Nov. 25, 2014

(54) METHODS OF MAKING REVERSIBLE CROSSLINKED POLYMERS AND RELATED METHODS

(75) Inventors: Mark W. Ellsworth, Dublin, CA (US); Stefanie M. Gravano-Doerffler, Union City, CA (US)

(73) Assignee: Tyco Electronics Corporation, Berwyn, PA (US)

( * ) Notice: Subject to any disclaimer, the term of this patent is extended or adjusted under 35 U.S.C. 154(b) by 503 days.

(21) Appl. No.: 12/460,350

(22) Filed: Jul. 17, 2009

(65) Prior Publication Data

US 2011/0015350 A1 Jan. 20, 2011

(51) Int. Cl.
*C08J 3/24* (2006.01)
*C08L 101/00* (2006.01)
*C07C 45/40* (2006.01)
*C08F 8/00* (2006.01)
C08J 11/10 (2006.01)
C08C 19/00 (2006.01)
C08L 9/00 (2006.01)
C08L 33/06 (2006.01)
C08L 23/08 (2006.01)

(52) U.S. Cl.
CPC . *C08F 8/00* (2013.01); *C07C 45/40* (2013.01); C08C 2019/09 (2013.01); *C08J 3/244* (2013.01); *C08L 101/00* (2013.01); *C08J 11/10* (2013.01); C08L 9/00 (2013.01); C08L 33/06 (2013.01); C08L 23/08 (2013.01)
USPC ............ 525/196; 525/326.2; 525/333.7; 525/410; 525/418; 525/537; 525/540

(58) Field of Classification Search
USPC ............ 525/326.1, 326.2, 326.3, 33.7, 334.1, 525/333.3, 329.1, 329.2, 329.3, 410, 418, 525/419, 537, 540, 196, 333.7
See application file for complete search history.

(56) References Cited

U.S. PATENT DOCUMENTS

| 5,039,737 A | 8/1991 | Parker et al. |
| 5,728,785 A | 3/1998 | Grubbs et al. |
| 2006/0241257 A1 | 10/2006 | Angeletakis |

FOREIGN PATENT DOCUMENTS

| DE | 10102086 A1 | 3/2002 |
| EP | 2028194 A1 | 2/2009 |
| WO | WO-2008027268 A2 * | 3/2008 |

OTHER PUBLICATIONS

Joly, Nicolas et al. Journal of Polymer Science Part A:Polymer Chemistry vol. 43 pp. 407-418 published Jan. 2005.*
N. Joly et al., "Crosslinking of Cellulose by Olefin Metathesis", *Journal of Carbohydrate Chemistry*, vol. 22, No. 1, Jan. 1, 2003, pp. 47-55.
International Search Report for International Application No. PCT/US2010/002007, dated Sep. 20, 2010.
Fuerstner et al., "Total Syntheses of (+)-Ricinelaidic Acid Lactone and of (−)-Gloeosporone Based on Transition-Metal-Catalyzed C—C Bond Formations", *J. Am. Chem. Soc.*, vol. 119, p. 9130-9136, 1997.
Sanford et al., "Mechanism and Activity of Ruthenium Olefin Metathesis Catalysts", *J. Am. Chem. Soc.*, vol. 123, p. 6543-6554, 2001.
Watson et al., "Solvent-Free Olefin Metathesis Depolymerization of 1,4-Polybutadiene", *Macromolecules*, vol. 33, p. 1494-1496, 2000.
Craig et al., "Highly Efficient Acyclic Diene Metathesis Depolymerization Using a Ruthenium Catalyst Containing a N-Heterocyclic Carbene Ligand", *Macromolecules*, vol. 34, p. 7929-7931.

* cited by examiner

*Primary Examiner* — Irina S Zemel
*Assistant Examiner* — Jeffrey Lenihan

(57) ABSTRACT

Methods are provided for making reversible crosslinked polymers. Exemplary methods comprise reacting first and second thermoplastic polymers having non-hindered olefins in the presence of a metathesis catalyst under conditions sufficient to form a crosslinked polymer. In certain embodiments, the methods comprise providing a crosslink promoting additive to improve the strength of the crosslinked polymer. In some embodiments, the methods comprise decrosslinking a crosslinked polymer through a metathesis or an ozonolysis reaction.

9 Claims, No Drawings

METHODS OF MAKING REVERSIBLE CROSSLINKED POLYMERS AND RELATED METHODS

TECHNICAL FIELD

The present disclosure relates to methods for making reversible crosslinked polymers. More particularly, the disclosure relates to methods for crosslinking and/or decrosslinking thermoplastic polymers.

BACKGROUND

Crosslinked polymers are known to increase thermal stability, toughness, and chemical resistance compared to their base, or uncrosslinked polymers. However, crosslinked polymers are also known to be intractable, making them difficult to reprocess or recycle. Therefore, there is a need for crosslinked polymers where the crosslinking elements can be reversed or removed (i.e., decrosslinked) when necessary.

Methods of forming recyclable polymers have included using oligomers capable of hydrogen bonding to form highly crosslinked networks, or highly crosslinked networks of polymers formed by reactive groups that can be thermally reversed or decomposed. However, these systems are limited by their moisture instability (in the case of the hydrogen bonded polymers) or limited by their upper use temperature. Due to these limitations, there is a need for improved methods of making reversible crosslinked polymers, including methods for crosslinking and decrosslinking polymers.

BRIEF SUMMARY

Embodiments of the present invention generally provide methods of crosslinking, and optionally, decrosslinking thermoplastic polymers.

In one embodiment, a method for making a reversible crosslinked polymer comprises providing first and second thermoplastic polymers each having at least one pendant olefin, where the pendant olefin is non-hindered. In some embodiments of this method, the first and second thermoplastic polymers have molecular weights of approximately 30,000 g/mol or greater. In some embodiments, the first and second polymers have an olefin content of less than approximately 30% by weight of the thermoplastic polymer. This method further comprises providing a first metathesis catalyst and reacting the first and second thermoplastic polymers in the presence of the metathesis catalyst under conditions sufficient to form a crosslinked polymer. In some embodiments of this method, the first metathesis catalyst is a ruthenium-based catalyst, a Grubbs First Generation-type catalyst, a Grubbs Second Generation-type catalyst, or a combination thereof. In some embodiments of this method, the first metathesis catalyst has a catalyst concentration between approximately 0.1 mol % and approximately 10 mol % per mol non-hindered olefin in the thermoplastic polymer. In some embodiments of this method, the reacting results in a crosslinking yield between approximately 50% and approximately 80%. In some embodiments of this method, the reacting results in an improved tensile strength over crosslinking by electron beam radiation.

In another embodiment, a method for making a reversible crosslinked polymer comprises providing first and second thermoplastic polymers each having at least one pendant olefin, where the pendant olefin is non-hindered. In some embodiments, the first and second polymers have molecular weights of approximately 30,000 g/mol or greater. In some embodiments, the first and second polymers each have an olefin content of less than approximately 30% by weight of the thermoplastic polymer. This method further comprises providing a first metathesis catalyst and reacting the first and second thermoplastic polymers in the presence of the metathesis catalyst under conditions sufficient to form a crosslinked polymer. This method further comprises providing a second metathesis catalyst and an alkene, and reacting the crosslinked polymer with the alkene (such as ethylene) in the presence of the second metathesis catalyst under conditions sufficient to decrosslink the crosslinked polymer, forming a decrosslinked polymer having a pendant olefin. In some embodiments of this method, the first and second metathesis catalysts are ruthenium-based catalysts, a Grubbs First Generation-type catalysts, a Grubbs Second Generation-type catalysts, or a combination thereof. In some embodiments of this method, the first and second metathesis catalysts each have catalyst concentrations between approximately 0.1 mol % and approximately 10 mol % per mol non-hindered olefin in the thermoplastic polymer. In some embodiments of this method, the reacting results crosslinking and decrosslinking yields between approximately 50% and approximately 90%. In some embodiments of this method, the reacting results in an improved tensile strength over crosslinking by electron beam radiation.

In another embodiment, a method for making a reversible crosslinked polymer comprises providing first and second thermoplastic polymers each having at least one pendant olefin, where the pendant olefin is non-hindered. In some embodiments, the first and second polymers have molecular weights of approximately 30,000 g/mol or greater. In some embodiments, the first and second thermoplastic polymers each have an olefin content of less than approximately 30% by weight of the thermoplastic polymer. In one embodiment, this method further comprises providing a metathesis catalyst and reacting the first and second thermoplastic polymers in the presence of the metathesis catalyst under conditions sufficient to form a crosslinked polymer. In another embodiment, this method further comprises providing ozone and reacting the crosslinked polymer with ozone under conditions sufficient to decrosslink the crosslinked polymer, forming a decrosslinked polymer having a pendant aldehyde. In some embodiments, this method may further comprise converting the pendant aldehyde on the decrosslinked polymer into a pendant olefin. In some embodiments of this method, the metathesis catalyst is a ruthenium-based catalyst, a Grubbs First Generation-type catalyst, Grubbs Second Generation-type catalyst, or combination thereof. In some embodiments of this method, the metathesis catalyst has a catalyst concentration between approximately 0.1 mol % and 10 mol % per mol non-hindered olefin in the thermoplastic polymer. In some embodiments of this method, the reacting results in crosslinking and decrosslinking yields between approximately 50% and approximately 90%. In some embodiments of this method, the reacting results in an improved tensile strength over crosslinking by electron beam radiation.

In still another embodiment, a method for making a reversible crosslinked polymer comprises providing first and second thermoplastic polymers each having at least one pendant olefin, where the pendant olefin is non-hindered. In some embodiments, the first and second polymers have molecular weights of approximately 30,000 g/mol or greater. In some embodiments, the first and second thermoplastic polymers each have an olefin content of less than approximately 30% by weight of the thermoplastic polymer. This method further comprises providing a first metathesis catalyst and a crosslink promoting additive, and reacting the first and second thermoplastic polymers in the presence of the metathesis catalyst and crosslink promoting additive under conditions sufficient to form a crosslinked polymer. In some embodiments of this method, the tensile strength of the crosslinked polymer is at least approximately 10% stronger than a similar crosslinked polymer without the crosslink promoting additive. In other embodiments of this method, the crosslink promoting additive improves the tensile strength by at least three times over an electron beam radiation reaction at 10 MRads having a similar amount of the crosslink promoting additive. In some embodiments of this method, the crosslink promoting additive is selected from the group consisting of: triallyl isocyanurate, trimethylolpropanetrimethacrylate, and combinations thereof. In some embodiments of this method, the crosslinked polymer is decrosslinked by either a metathesis reaction or ozonolysis reaction mechanism.

In yet another embodiment, a method for making a reversible crosslinked polymer comprises providing a crosslinked thermoplastic polymer, a metathesis catalyst, and an alkene, and reacting the crosslinked polymer with the alkene in the presence of the metathesis catalyst under conditions sufficient to decrosslink the crosslinked polymer and form a decrosslinked polymer having a pendant olefin. In some embodiments of this method, the metathesis catalyst is a ruthenium-based catalyst selected from the group consisting of: Grubbs First Generation-type catalysts, Grubbs Second Generation-type catalysts, and combinations thereof. In some embodiments of this method, the amount of metathesis catalyst is between approximately 0.1 mol % and approximately 10 mol % catalyst per mol non-hindered olefin in the thermoplastic polymer. In some embodiments of this method, the decrosslinking reaction results in a decrosslinking yield of at least approximately 50%.

In another embodiment, a method for making a reversible crosslinked polymer comprises providing a crosslinked thermoplastic polymer and ozone, and reacting the crosslinked polymer with the ozone under conditions sufficient to decrosslink the crosslinked polymer and form a decrosslinked polymer having a pendant aldehyde. In some embodiments, the method further comprises converting the pendant aldehyde on the decrosslinked polymer into a pendant olefin. In some embodiments of this method, the decrosslinking reaction results in a decrosslinking yield of at least approximately 50%.

DETAILED DESCRIPTION

As used herein, terms such as "typically" are not intended to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

As used herein, the term "thermoplastic polymer" refers to a polymer that softens when exposed to heat and returns to a more rigid condition when cooled. These polymers can typically go through repeated melting and freezing cycles, and can be reshaped upon reheating. Thermoplastic polymers typically are high-molecular weight polymers, have a chain length capable of forming entanglements, or are longer than a persistence length (i.e., the length in which correlations in the direction of the tangent are lost). In certain embodiments, the thermoplastic polymer has a molecular weight greater than approximately 30,000 g/mol. These polymers may be amorphous or semi-crystalline in structure in their solid state. Examples of thermoplastic polymers include, but are not limited to compounds having a backbone containing: polyethylene, polypropylene, acrylonitirile butadiene styrene, acrylic, celluloid, cellulose acetate, cycloolefin copolymer, ethylene vinyl acetate, ethylene vinyl alcohol, fluorinated ethylene propylene, fluoroplastics, perfluoroalkoxy copolymer, polyacetal, polyacrylates, polyacryonitrile, polyamine, polyamide-imide, polyaryletherketone, polybutadiene, polybutylene, polybutylene terephthalate, polycaprolactone, polychlorotrifluoroethylene, polyethylene terephthalate, polycyclohexylene dimethylene terephthalate, polycarbonate, polyhydroxyalkanoates, polyketone, polyester, polyetheretherketone, polyetherketoneketone, polyetherimide, polyethersulfone, polyethylenechlorinates, polyethylene tetrafluoroethylene, polyimide, polylactic acid, polymethylpentene, polyphenylene oxide, polyphenylene sulfide, polyphthalamide, polystyrene, polysulfone, polytrimethylene terephthalate, polyurethane, polyvinyl acetate, polyvinyl chloride, polyvinylidene chloride, styrene-acrylonitrile, and combinations or copolymers thereof. In one embodiment, the thermoplastic polymer has a polyethylene backbone. In another embodiment, the thermoplastic polymer has an acrylic backbone. In still another embodiment, the thermoplastic polymer has a polymethyl methacrylate backbone. In yet another embodiment, the thermoplastic polymer has a butadiene backbone.

As used herein, the term "pendant chain" or "pendant olefin" refers to a side group containing an olefin, where the side group is attached to the backbone of the thermoplastic polymer. Unless indicated otherwise, the term "thermoplastic polymer" includes the pendant chain or pendant olefin. In certain embodiments, the pendant chain is an alkene group having a chain length of at least 5 carbon atoms. And, in further embodiments, the olefin is a terminal olefin.

As used herein, the term "non-hindered olefin" refers to an olefin positioned on the pendant chain of the polymer in an accessible location, capable of undergoing a metathesis reaction with another non-hindered olefin. In certain embodiments, the non-hindered olefin is a terminal olefin.

As used herein, the term "uncrosslinked polymer" refers to a starting polymer compound or "base" thermoplastic polymer that exists prior to undergoing a metathesis reaction in which a crosslinked polymer is produced.

As used herein, the terms "crosslink," "crosslinked," and "crosslinking" refer to a metathesis reaction, or product thereof, between thermoplastic polymers having non-hindered olefin, where the polymers are joined and an olefin byproduct is produced. In certain embodiments, the non-hindered olefins are terminal olefins and the olefin byproduct is ethylene.

As used herein, the terms "decrosslink," "decrosslinked," and "decrosslinking" refer to a metathesis or an ozonolysis reaction between a crosslinked polymer and either: (i) an olefin, such as ethylene, or (ii) ozone, in which the crosslinked polymer is unjoined. In one embodiment, the starting polymers with pendant olefins are reformed during the decrosslinking reaction, and the crosslinking process can recommence when desired.

As used herein, the term "crosslinking yield" refers to the weight of the crosslinked polymers divided by the weight of the starting base, uncrosslinked polymer.

As used herein, the term "decrosslinking yield" refers to the weight of the decrosslinked polymers divided by the weight of the starting amount of crosslinked polymer.

In developing improved methods for crosslinking and decrosslinking thermoplastic polymers, the inventors have discovered that catalytic methods are advantageous for crosslinking and decrosslinking. For example, catalytic methods allow for a degree of control over crosslinking and decrosslinking, as the reactions are only activated with the addition of the catalyst and/or reactive reagents. Therefore, the base (uncrosslinked) polymer can be stored and processed much like standard polymers, and the crosslinking catalyst can then be added when needed. Likewise, the crosslinked polymer will be thermally and hydrolytically stable until a catalyst and/or reactive reagent is added to undo the crosslinking (i.e. to decrosslink).

Applications for these methods include, without limitation, the recycling of polymers, particularly related to component end-of-life reclamation and scrap material recovery and reuse. In certain embodiments, catalytic crosslinking and decrosslinking may be used to replace electron beam radiation or peroxide crosslinking for heat shrink tubing and insulated wire products, particularly for thick wall tubing or thick wall insulation where electron beam radiation cannot penetrate through the full thickness, and where peroxide chemistry does not offer enough control over the crosslinking process. In other embodiments, catalytic crosslinking and decrosslinking may be used for adhesive lined heat shrink tubing, which may eliminate the need for special additives in the adhesive that are normally used to prevent crosslinking or degradation of the adhesive during electron beam crosslinking of the outer material. In other embodiments, catalytic crosslinking and decrosslinking may be used with chemically removable adhesives and sealants. Numerous other applications are also possible.

In certain embodiments, the thermoplastic polymers comprise at least one pendant olefin or pendant chain extending from the polymer backbone. In certain embodiments, the pendant olefin-containing thermoplastic polymer can be prepared by reacting an acid-containing polymer with an olefin-containing alcohol under conditions sufficient to convert the acid functionality of the polymer to a pendant olefin-containing functionality. In one particular example, polyethylene-co-acrylic acid can be reacted with an olefin-containing alcohol under conditions sufficient to convert the acrylic acid functionality to a pendant olefin-containing functionality, as shown below in (I):

In another example, methyl methyacrylate can be reacted with an alpha-olefin methylacrylic ester which was synthesized by reacting methacrylic acid with an olefin-containing alcohol under conditions sufficient to produce an acrylic based polymer, such as the example shown below in (II):

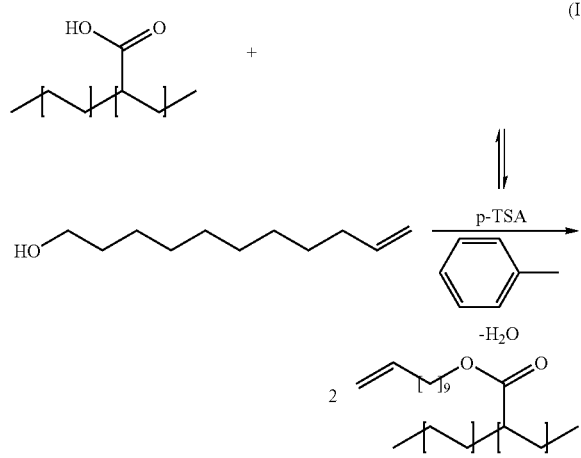

Although there is no effective limit to the olefin content of a thermoplastic polymer and the ability to crosslink a polymer with high olefin content, the inventors have found that the crosslinking of high olefin content polymers can result in highly networked, brittle materials. Additionally, the crosslinking of high olefin content polymers may result in a significant percentage of unreacted olefin, which could further degrade properties and interfere with the reverse crosslinking (i.e., decrosslinking) reaction. Therefore, in certain embodiments, the olefin content in the thermoplastic polymer is less than approximately 30% by weight of the thermoplastic polymer. In still other embodiments, the olefin content is less than approximately 20% by weight. In still other embodiments, the olefin content is less than approximately 10% by weight. In still other embodiments, the olefin content is less than approximately 5% by weight. In one embodiment, the olefin content is between approximately 0.1% by weight and approximately 30% by weight. In another embodiment, the olefin content is between approximately 0.1% by weight and approximately 10% by weight. In still another embodiment, the olefin content is between approximately 1% by weight and approximately 10% by weight.

The olefin content of a polymer can be adjusted during formation of the thermoplastic polymer with pendant olefins. In certain embodiments, a thermoplastic polymer with a pendant olefin, such as the methyl methacrylate example shown below in (III), may have a varying percent by weight of olefin content based on the values of n, x, and y. For instance, the polymer has approximately 1% by weight olefin content when x=1, y=310, n=9, while the polymer has approximately 10% by weight olefin content when x=38, y=338, and n=9.

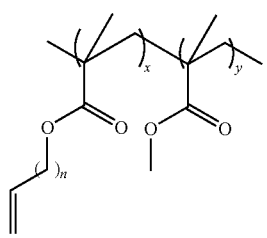

(III)

Through variations in the amount of olefin, and the amounts of the crosslinkable monomer (x) and non-crosslinkable monomer (y), the resulting crosslinked polymer can have different tensile strengths and can be utilized in different applications. For example, the methyl methacrylate containing polymer shown above in (III) can be varied by adjusting the ratio of monomers x and y, as described in the reaction above in (II). In certain embodiments, applications for the crosslinked polymer include, for example, crosslinked wire, tubing, connector housings and in any other applications in which increased structural integrity is desired.

Crosslinking is facilitated by a pendant olefin that is non-hindered. In one embodiment, the non-hindered olefin is a terminal olefin, as shown in the pendant olefin on the polymethyl methacrylate compound (III) above. In one embodiment, the chain length of the pendant olefin is five (5) carbon atoms or greater (i.e., as shown in the compound (III) above, n is 3 or greater). In other embodiments, for example, the non-hindered pendant olefin contains at least 6, 7, 8, 9, 10, or 11 carbon atoms (i.e., n=4, 5, 6, 7, 8, 9, or greater).

In developing a catalytic reaction to crosslink thermoplastic polymers, the inventors have discovered that crosslinking can be achieved through metathesis chemistry. Metathesis reactions are catalytic reactions generally known in the art that involve the interchange of alkylidene units among compounds containing one or more double bonds (e.g., olefinic compounds) via the formation and cleavage of the carbon-carbon double bonds. The metathesis reaction is typically achieved in the presence of a metathesis catalyst. Metathesis catalysts are well known in the art, as well as the reaction conditions in which the metathesis reaction takes place.

In one embodiment, the metathesis catalyst is a ruthenium-based metathesis catalyst. In another embodiment, the metathesis catalyst is a first-generation Grubbs' catalyst ("G1").

In still another embodiment, the metathesis catalyst is a second-generation Grubbs' catalyst ("G2"). Ruthenium-based, first- and second-generation Grubbs' catalysts are well known in the art, as well as typical metathesis reaction conditions sufficient to facilitate the metathesis reaction. Exemplary catalysts and reaction conditions are described in U.S. Pat. Nos. 5,312,940; 5,969,170; 6,077,808; 6,111,121; 6,426,419; 7,102,047; and 7,329,759, herein incorporated by reference. These types of metathesis catalysts are available from Materia, Inc., Pasadena, Calif., USA.

In certain embodiments, during the crosslinking reaction, thermoplastic polymers link together and produce an olefin byproduct (e.g. ethylene gas). The loss of the olefin byproduct is a driving force of the reaction. Additionally, in some embodiments, during decrosslinking (discussed in greater detail below), the addition of olefin gas (e.g. ethylene) is a driving force of the reaction. An exemplary reaction mechanism is shown below in (IV):

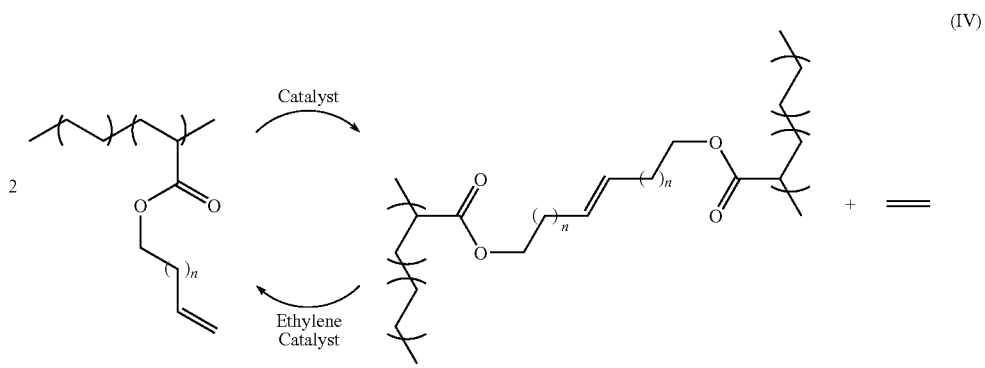

(IV)

The amount of metathesis catalyst required to crosslink a thermoplastic polymer varies. In one embodiment, under conditions sufficient for a metathesis reaction, the amount of metathesis catalyst added to facilitate the crosslinking reaction is less than approximately 10 mol % of catalyst per mol non-hindered olefin in the thermoplastic polymer. In another embodiment, the amount of catalyst is less than approximately 5 mol %. In still another embodiment, the amount of catalyst is less than approximately 1 mol %. In yet another embodiment, the amount of catalyst required to crosslink is less than approximately 0.5 mol %. In other embodiments, the amount of catalyst is between approximately 0.01 mol % and approximately 10 mol %; or between approximately 0.1 mol % and approximately 5 mol %; between approximately 0.1 mol % and approximately 1 mol %. In one embodiment, the amount of catalyst is approximately 0.3 mol %.

In certain embodiments, the metathesis crosslinking reaction of thermoplastic polymers results in a crosslinking yield of at least approximately 50%. In other embodiments, the crosslinking yield is at least approximately 60%, 65%, 70%, or 75%. In other embodiments, the crosslinking yield is between approximately 50% and approximately 80%; between approximately 60% and approximately 80%; or between approximately 70% and approximately 80%.

In comparison to alternative crosslinking methods known in the art, such as electron beam radiation, improvements in crosslink density can be achieved through the embodiments of the present invention. Improvements in crosslink density can be measured by studying the improvement in the tensile strength of the modulus at 100% elongation (M-100), where an improvement in strength corresponds to an improvement in crosslink density. In one embodiment, metathesis catalytic crosslinking has an improvement in strength of at least approximately two times the strength obtained by electron beam radiation crosslinking. In other embodiments, metathesis crosslinking has an improvement in strength of at least approximately three times, at least approximately five times, or at least approximately ten times the strength obtained by electron beam radiation crosslinking.

In certain embodiments, crosslinking density and tensile strength may be further improved through the addition of a crosslink promoting additive. In one embodiment, the addition of a crosslink promoting additive can improve the strength by at least approximately 10% when compared to similar crosslink metathesis reaction conditions without the additive. In another embodiment, the addition of the additive can improve the strength by at least approximately 20%.

The amount of crosslink promoting additive is also variable. In one embodiment, the amount of crosslink promoting additive added to the metathesis reaction is between approximately 0.1% by weight and approximately 10% by weight of the additive in relation to the thermoplastic polymer. In another embodiment, the amount of additive is between approximately 0.1% by weight and approximately 1% by weight of additive per weight thermoplastic polymer.

In certain embodiments, various types of promoting additives may be used to improve the density and strength of the crosslinked polymer. In certain embodiments, promoting additives such as triallyl isocyanurate (TAIC), trimethylolpropanetrimethacrylate (TMPTM), or combinations thereof may be used to improve density and strength. In certain embodiments, less than approximately 1%, 2%, 3%, 4%, or 5% by weight of an additive is added in relation to the thermoplastic polymer. In another embodiment, approximately 1% by weight additive is added. In other embodiments, between approximately 0.01% by weight and approximately 5% by weight, between approximately 0.01% by weight and approximately 1% by weight, between approximately 0.1% by weight and approximately 5% by weight, or between approximately 0.1% by weight and approximately 1% by weight of an additive is added. In one embodiment, TAIC is used as the additive. TAIC is supplied by Mitsubishi International Corporation, New York, N.Y., USA. In another embodiment, TMPTM is used as the additive. TMPTM is supplied by Esstech, Inc., Essington, Pa., USA.

In addition to crosslinking the thermoplastic polymer, in certain embodiments, it is desirable to recycle the polymers, helping to minimize the costs of new materials. The inventors have discovered embodiments in which the crosslinked polymers can be recycled or decrosslinked through a cleaving reaction, wherein the crosslinked polymer is split apart along the non-hindered olefin. In one embodiment, the cleaving occurs through a cross-metathesis catalytic reaction, wherein the crosslinked thermoplastic polymer is reacted with an olefin in the presence of a metathesis catalyst. In another embodiment, the cleaving occurs through an ozonolysis reaction, wherein the crosslinked thermoplastic polymer is reacted with ozone.

As previously discussed, metathesis catalysts are well known in the art, as well as the reaction conditions in which the metathesis reaction takes place. Similar metathesis catalysts and reaction conditions can be used in decrosslinking as were used in the crosslinking of the thermoplastic polymers. In one embodiment, the metathesis catalyst is a ruthenium-based metathesis catalyst. In another embodiment, the metathesis catalyst is a first-generation Grubbs' catalyst. In still another embodiment, the metathesis catalyst is a second-generation Grubbs' catalyst. In certain embodiments, the same type of catalyst is used in the crosslinking and decrosslinking reactions.

In certain embodiments, decrosslinking occurs when a crosslinked polymer is reacted with an olefin resulting in the regeneration of two thermoplastic polymers having pendant olefins. One such reaction mechanism is shown above in (IV).

In one embodiment, the olefin used in the decrosslinking reaction is an alkene. In another embodiment, the alkene used in the decrosslinking reaction is ethylene, which facilitates the production of uncrosslinked polymers having pendant terminal olefins. In other embodiments, other alkenes may be used in the decrosslinking reaction, but may not reproduce uncrosslinked polymers comprised entirely of polymers with pendant terminal olefins.

The amount of metathesis catalyst required to decrosslink a thermoplastic polymer varies. In one embodiment, under typical metathesis reaction conditions, the amount of metathesis catalyst to facilitate the decrosslinking reaction is less than approximately 10 mol % of catalyst per mol non-hindered olefin in the thermoplastic polymer. In certain embodiments, the amount of catalyst is less than approximately 5 mol %; less than approximately 1 mol %; or less than approximately 0.5 mol %. In some embodiments, the amount of catalyst is between approximately 0.01 mol % and approximately 10 mol %; between approximately 0.1 mol % and approximately 5 mol %; or between approximately 0.1 mol % and approximately 1 mol %. In one embodiment, the amount of catalyst is approximately 0.3 mol %.

In certain embodiments, the metathesis decrosslinking reaction of a thermoplastic polymer results in a decrosslinking yield of at least approximately 50%. In some embodiments, the decrosslinking yield is at least approximately 60%, 65%, 70%, 75%, 80%, or 85%. In other embodiments, the decrosslinking yield is between approximately 50% and approximately 90%, between approximately 60% and approximately 90%, between approximately 70% and approximately 90%, or between approximately 80% and approximately 90%.

In certain embodiments, a crosslinked polymer is decrosslinked through an ozonolysis reaction mechanism, an example of which is shown below in (V). Ozonolysis is a chemical reaction generally known in the art. Ozonolysis is the reaction of an olefin with ozone under conditions sufficient to cleave an unsaturated carbon-carbon bond and replace it with a double bond to oxygen. Typical reaction conditions for ozonolysis are well-known in the art, as described in U.S. Pat. Nos. 3,481,954; 3,868,392; and 4,085,127, herein incorporated by reference.

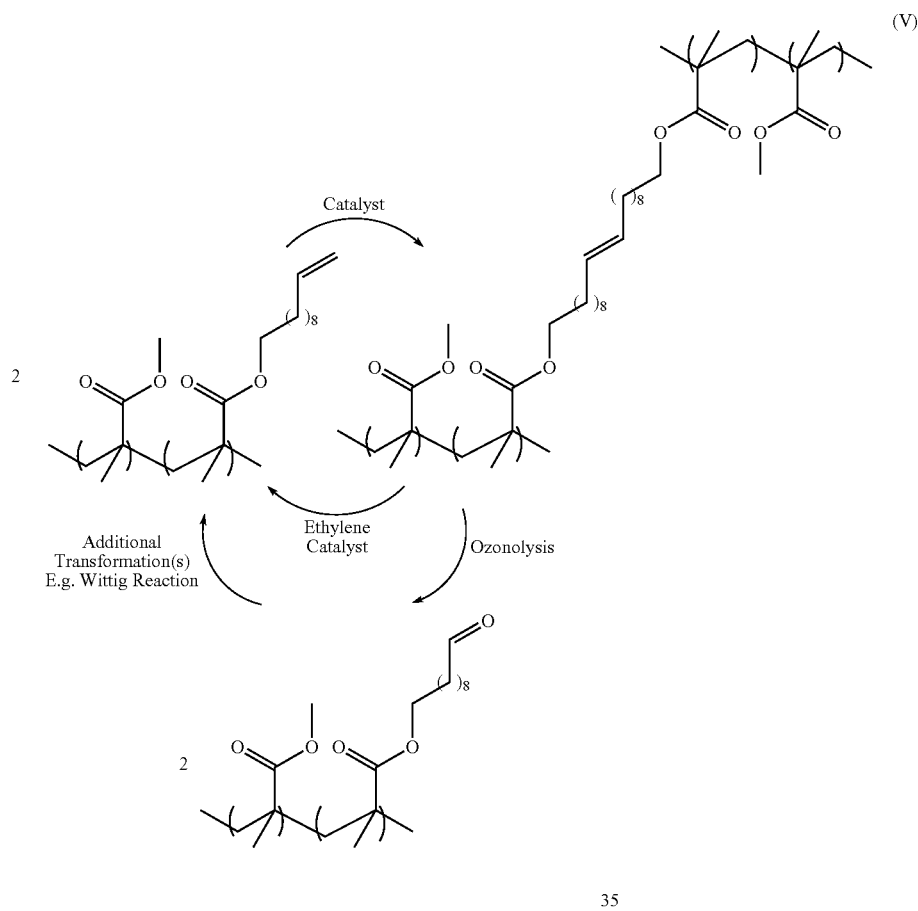

In certain embodiments, following an ozonolysis reaction in which a crosslinked polymer is decrosslinked, an additional transformation step such as a Wittig reaction (e.g., reacting the aldehyde with a phosphonium ylide, such as a triphenyl phosphonium ylide) is used to convert an aldehyde of a thermoplastic polymer to yield its olefinic form, as shown in (V).

In certain embodiments, the ozonolysis decrosslinking reaction of a thermoplastic polymer results in a decrosslinking yield of at least approximately 50%. In other embodiments, the decrosslinking yield can be at least approximately 60%, 65%, 70%, or 75%. In certain embodiments, the decrosslinking yield can be between approximately 50% and approximately 80%, between approximately 60% and approximately 80%, or between approximately 65% and approximately 75%.

EXAMPLES

In various examples discussed below, methyl methacrylate (MMA) polymers are used to exemplify different embodiments of crosslinking and decrosslinking thermoplastic polymers. The methyl methacrylate polymers had any inhibitors removed and were dried and distilled prior to use in polymerization reactions. Ruthenium-based catalysts (e.g., first and second generation Grubbs' catalysts ("G1" and "G2")) were stored under inert conditions. All other reagents were used as received. Modified polymers were cryogenically ground by cooling with liquid $N_2$ using a Brinkmann ZM-200 mill fitted with a ring sieve before being used in crosslinking reactions.

Example 1

Typical Alkene Functionalization of poly(ethylene-co-acrylic acid) (EAA)

EAA (20.0 g (4.0 g acid), 55.6 mmol) containing 5%, 10% or 20% acrylic acid by weight was added to a 3-neck round bottom flask affixed with a mechanical stirrer and Dean-Stark adapter and solvated in toluene (300 ml) over 2 h. P-toluene sulfonic acid (p-TSA) (1.05 g, 5.56 mmol) and unecene-1-ol (12.2 ml, 61.1 mmol) were added and the mixture was heated to reflux for 12 h. The product was precipitated in MeOH (2 L) and dried to yield 24.4 g (86% yield) of a white, rubbery material. This material was cryogenically ground (5 mm aperture size) for further reactions.

Example 2

Typical Alkene Functionalization of poly(methyl methacrylate) (MMA)

Monomer synthesis. In a 3 neck round bottom flask, methacrylic acid (51.4 g, 0.515 mol) and benzene (60 ml) were combined. P-TSA (0.90 g, 2.6 mmol), hydroquinone (1.56 g, 13.6 mmol) and undecene-1-ol (25.8 g, 0.150 mol) were added into the flask and a Dean Stark adapter was attached. The reaction was heated at reflux overnight. The benzene was removed from the solution by rotary evaporation at reduced pressure and ether (200 ml) was added. NaHCO$_3$ (50 g) was added to the ether solution to remove any excess methacrylic acid. The product was decanted from the NaHCO$_3$ and washed with H$_2$O (200 ml) 3 times, with 5% by weight NaHCO₃ (200 ml) solution 3 times, and again with H₂O (200 ml) 3 times. The product was dried over MgSO₄ and the ether was removed by rotary evaporation. The product was distilled at 110° C. at 150 mTorr to yield 18.3 g (51% yield) of undec-10-enyl methacrylate.

Copolymerization of methyl methacrylate and undec-10-enyl methacrylate. Azobisisobutyronitrile (AIBN) (36.8 mg, 0.21 mmol) was added into a 100 ml Schlenk flask and put under inert conditions by purging with dry $N_2$. Butyl acetate (37 ml) was added to the flask and bubbled with dry $N_2$ followed by the addition of undec-10-enyl methacrylate (UMA) (1.1 ml, 4.05 mmol) and methyl methacrylate (4.0 ml, 37.6 mmol). The reaction was heated to 70° C. under a slightly positive $N_2$ atmosphere overnight. The polymer was precipitated in MeOH (250 ml), filtered and dried under vacuum to yield 4.25 g of solid white of poly(MMA-co-UMA) which is 90% MMA and 10% UMA (89% yield).

Example 3

Typical Crosslinking Reaction

The poly(methyl methacrylate-co-undec-10-enyl methacrylate) (0.50 g, 11.7 μmol, 0.439 mmol C=C) was put into a 10 ml round bottom flask and charged with $N_2$. Dry $CH_2Cl_2$— (4.0 ml) was added to dissolve the polymer. A second-generation Grubbs catalyst (G2) (37.2 mg, 0.0439 mmol, 10 mol %) was added and a reddish brown gel formed. Table 1 below includes exemplary alternative variations of crosslinking reactions.

Example 4

Typical Metathesis Decrosslinking Reaction

In a 10 ml round bottom flask of crosslinked poly(MMA-co-UMA) (0.50 g, 11.7 μmol, 0.439 mmol C=C) the gel was swollen with $CH_2Cl_2$ (7 ml) and stirred. Grubbs G2 (37.2 mg, 0.0439 mmol, 10 mol %) was added and a balloon of ethylene was used to saturate the gel/catalyst slurry with ethylene. The reaction was allowed to stir overnight and the resulting dark brown solution of polymer and solvent was precipitated in MeOH (20 ml), filtered and dried to yield 0.473 g (88% yield) of decrosslinked polymer. Table 1 below includes alternative variations of metathesis decrosslinking reactions.

Example 5

Typical Ozonolysis Decrosslinking Reaction

In a 10 ml round bottom flask crosslinked poly(MMA-co-UMA) gel (0.56 g, 13.3 μmol, 0.501 mmol C=C) was swollen with $CH_2Cl_2$ (7 ml), broken into smaller chunks, chilled to −78° C. and stirred. The solution was purged with $O_2$ for 5 minutes followed by purging with $O_3$ for 15 minutes. During the exposure to $O_3$, the gel was solvated in the solution. The solution was then bubbled with $O_2$ for 1 h to ensure that no $O_3$ remained, and a few drops of $Me_2S$ were added to quench any residual $O_3$. The solution was precipitated in MeOH (20 ml), filtered and dried to yield 0.365 g (65% yield) of aldehyde functionalized decrosslinked polymer.

TABLE 1

Parameters for various crosslinking and decrosslinking reactions.

| # | Polymer | Olefin content | Type, Amount of catalyst | Solvent | Reaction Time | Crosslink | Amt. of Catalyst | Decrosslink |
|---|---------|----------------|--------------------------|---------|---------------|-----------|------------------|-------------|
| 1 | 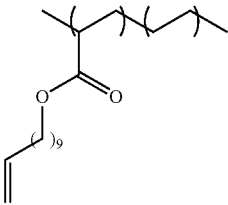 | 5% (by wt) | G1, 6 mol % | $CH_2Cl_2$ | Overnight | Yes | | 67% |
| 2 | 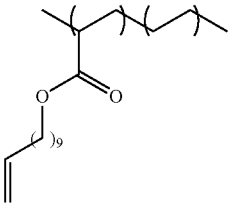 | 10% (by wt) | G1, 3 mol % | $CH_2Cl_2$ | Overnight | Yes | | 74% |
| 3 | 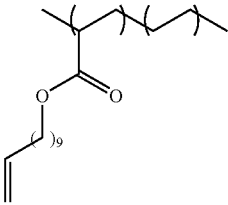 | 20% (by wt) | G1, 1 mol % | $CH_2Cl_2$ | 20 min | Yes | | 76% |

TABLE 1-continued

Parameters for various crosslinking and decrosslinking reactions.

| # | Polymer | Olefin content | Type, Amount of catalyst | Solvent | Reaction Time | Crosslink | Amt. of Catalyst | Decrosslink |
|---|---|---|---|---|---|---|---|---|
| 4 | 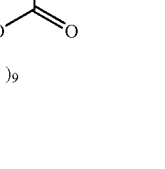 | 20% (by wt) | G1, 1 mol % | 1,2,4-trichlorobenzene | 5 min | Yes 75% | | |
| 5 | 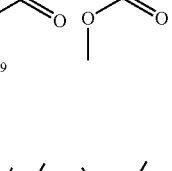 | x = 36, y = 36 | G2, 15 mol % | THF | 1 h | Yes Completely Insoluble | | |
| 6 | 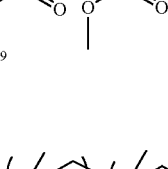 | x = 338, y = 376 | G2, 10 mol % | CH$_2$Cl$_2$ | 2 min | Yes Completely Insoluble | 10 mol % G2 | Yes 89% |
| 7 |  | x = 338, y = 376 | G1, 10 mol % | CH$_2$Cl$_2$ | 1.5 h | Yes Completely Insoluble | 10 mol % G1 | Yes 51% |
| 8 |  | x = 66, y = 268 | G2, 5 mol % | CH$_2$Cl$_2$ | Overnight | No | | |
| 9 |  | x = 338, y = 376 | G2, 5 mol % | CH$_2$Cl$_2$ | 20 min | Yes Completely Insoluble | | |

TABLE 1-continued

Parameters for various crosslinking and decrosslinking reactions.

| # | Polymer | Olefin content | Type, Amount of catalyst | Solvent | Reaction Time | Crosslink | Amt. of Catalyst | Decrosslink |
|---|---------|----------------|--------------------------|---------|---------------|-----------|------------------|-------------|
| 10 | (structure) | $x = 1$, $y = 311$ | G2, 100 mol % | $CH_2Cl_2$ | Overnight | No | | |
| 11 | (structure) | $x = 38$, $y = 343$ | G2, 10 mol % | $CH_2Cl_2$ | Overnight | Yes Completely Insoluble | | |
| 12 | (structure) | $x = 30$, $y = 324$ | G2, 5 mol % | $CH_2Cl_2$ | 4 h | Yes Completely Insoluble | | |
| 13 | (structure) | $x = 3$, $y = 719$ | G2, 5 mol % | $CH_2Cl_2$ | 4 h | Yes Completely Insoluble | | |
| 14 | (structure) | $x = 338$, $y = 376$ | G2, 5 mol % | $CH_2Cl_2$ | 20 min | Yes Completely Insoluble | G2, 5 mol % | Yes 54% |
| 15 | (structure) | $x = 338$, $y = 376$ | G2, 5 mol % | $CH_2Cl_2$ | 20 min | Yes Completely Insoluble | $O_3$ | Yes 65% |

TABLE 1-continued

Parameters for various crosslinking and decrosslinking reactions.

| | | | Crosslinking Reaction | | | | Decrosslinking Reaction | |
| | | | | Type, Amount | | | | |
| # | Polymer | Olefin content | of catalyst | Solvent | Reaction Time | Crosslink | Amt. of Catalyst | Decrosslink |
|---|---|---|---|---|---|---|---|---|
| 16 | | 55% 1,2-butadiene | G2, 0.1 mol % | none | Overnight | Yes | | |

As seen in Table 1, thermoplastic polymers are capable of crosslinking and decrosslinking under a variety of different conditions. As shown in experiment numbers 8, 10, and 11, crosslinking was successful when the olefin was not hindered (Experiment 11), but not when the olefin in the methyl methacrylate polymer was hindered (Experiments 8 and 10). In Experiment 11, when the pendant chain length was 5 carbon atoms, the terminal olefin was non-hindered and the crosslinking was successful.

As seen in Table 1, crosslinking was successful for both first generation Grubbs' catalysts (G1) and second generation Grubbs' catalysts (G2) at varying concentration amounts, including as low as 0.1 mol % G2 catalyst in Experiment 16. The crosslinking yield was approximately 76% in Experiment 3. In other experiments, the yield % was not calculated because the metathesis reaction product was insoluble and incapable of determining a yield percentage.

Table 1 also shows that varying amounts (% by weight) of olefin content in the polymer were capable of successfully crosslinking a non-hindered olefin polymer. For example, Experiment 13 shows that a low amount of olefin (approaching 1% by weight) in the thermoplastic polymer is still capable of crosslinking through a metathesis catalytic reaction.

Table 1 also shows that a variety of solvents such as dichloromethane ($CH_2Cl_2$), tetrahydrofuran (THF), and 1,2,4-trichlorobenzene, for example, were acceptable in achieving crosslinking of the thermoplastic polymers.

Regarding decrosslinking, the experimental results in Table 1 also show that both ozonolysis (Experiment 15) and metathesis G1 and G2 catalytic reactions (Experiments 6, 7, and 14) were successful in decrosslinking a crosslinked thermoplastic polymer. Decrosslinking yields were shown as high as 89% for the metathesis-based reaction (Experiment 6).

Example 6

Typical Crosslinking Additives

Approximately 1% by weight of a crosslinking promoting additive (TAIC or TMPTM) was added prior to the crosslinking reaction, such as the reaction described in Example 3. In this example, a semi-crystalline polyethylene olefin, shown below, was used in the various crosslinking reactions:

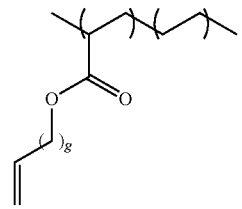

A determination was made as to whether the additive improved crosslinking efficiency, as defined by the crosslinking density and tensile strength of the modulus at 100% elongation (M-100), where an improvement in strength corresponds to an improvement in crosslink density. Comparisons between electron beam crosslinking and metathesis crosslinking (with or without a promoting additive) are shown below in Table 2.

TABLE 2

Comparison of electron beaming, catalytic crosslinking and the addition of a promoting additive on the modulus at 100% elongation.

| Beam Dose (MRads) | Additive (% by wt) | Catalyst | M-100 (psi) |
|---|---|---|---|
| 5 MRads | 1% TAIC | None | 18 |
| 10 MRads | 1% TAIC | None | 72* |
| 25 MRads | 1% TAIC | None | 315* |
| 50 MRads | 1% TAIC | None | 457* |
| None | None | 0.3 mol % | 254* |
| None | 1% TAIC | 0.3 mol % | 309* |
| None | 1% TMPTM | 0.3 mol % | 544* |

*Value extrapolated from the Modulus at 30% elongation

Table 2 shows that a catalytic crosslinking (with 0.3 mol % metathesis catalyst) with no promoting additive has more than a 3× improvement in strength over a 10 MRad beam dose and greater than 14× improvement over a 5 MRad beam dose. Additionally, catalytic crosslinking with no promoting additive was comparable to a high electron beam dose (25 MRads) with 1% by weight promoting additive. Catalytic crosslinking with a promoting additive further increased the strength over beam radiation or catalytic crosslinking without a promoting additive. For example, 0.3 mol % catalyst plus 1% by weight TAIC resulted in (i) a comparable strength in relation to a high, 25 MRad dose, (ii) more than a 4× improvement in strength over a 10 MRad beam dose, and (iii) a 20% improvement in strength over catalytic crosslinking without a promoting additive. Catalytic crosslinking with 1% by weight TMPTM resulted in: (i) approximately a 20% improvement in strength over a 25 MRad dose, (ii) more than a 7× improvement in strength over a 10 MRad beam dose, and (iii) more than a 2× improvement in strength over catalytic crosslinking without a promoting additive.

Example 7

Typical Catalytic Crosslinking with Bulk Polymer

A plaque of neat modified EAA (16.3 g, 14.5 mmol C═C) was pressed at 75° C. with 30,000 lbF and then treated with Grubbs G1 Ru catalyst (0.1 to 0.5 mol %). The plaque was folded and passed 15 times through a 2-roll mill which was not heated above room temperature (RT). The plaque itself did warm from RT to ~35° C. due to the shear of the mixing. The plaque was then cured at 75° C. for 30 min to complete the crosslinking reaction. This system is applicable to any modified polymer that is roll mill processable and is not heated above the temperature at which the crosslinking catalyst activates.

Although examples have been described herein, it should be appreciated that any subsequent arrangement designed to achieve the same or similar purpose may be substituted for the specific examples shown. This disclosure is intended to cover any and all subsequent adaptations or variations of various examples. Combinations of the above examples, and other examples not specifically described herein, may be apparent to those of skill in the art upon reviewing the description.

The Abstract is provided with the understanding that it will not be used to interpret or limit the scope or meaning of the claims. In addition, in the foregoing Detailed Description, various features may be grouped together or described in a single example for the purpose of streamlining the disclosure. This disclosure is not to be interpreted as reflecting an intention that the claimed examples require more features than are expressly recited in each claim. Rather, as the following claims reflect, inventive subject matter may be directed to less than all of the features of any of the disclosed examples. Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other examples, which fall within the true spirit and scope of the description. Thus, to the maximum extent allowed by law, the scope is to be determined by the broadest permissible interpretation of the following claims and their equivalents, and shall not be restricted or limited by the foregoing detailed description.

What is claimed is:

1. A method for making a reversible crosslinked polymer comprising:
   providing a mixture of polymers consisting of first and second semicrystalline thermoplastic polymers, each having at least one pendant olefin, wherein the pendant olefin is non-hindered, and wherein (a) each of the first and second polymers has an olefin content of less than approximately 30% by weight, and (b) each of the first and second polymers includes a backbone selected from the group consisting of: polyethylene, polypropylene, acrylonitrile butadiene styrene, acrylic acid and derivatives, cycloolefin copolymer, ethylene vinyl acetate, ethylene vinyl alcohol, fluorinated ethylene propylene, fluoroplastics, perfluoroalkoxy copolymer, polyacetal, polyacrylates, polyacrylonitrile, polyamine, polyamideimide, polyaryletherketone, polybutadiene, polybutylene, polybutylene terephthalate, polycaprolactone, polychlorotrifluoroethylene, polyethylene terephthalate, polycyclohexylene dimethylene terephthalate, polycarbonate, polyhydroxyalkanoates, polyketone, polyester, polyetheretherketone, polyetherketoneketone, polyetherimide, polyethersulfone, polyethylenechlorinates, polyethylene tetrafluoroethylene, polyimide, polylactic acid, polymethyl methacrylate, polymethylpentene, polyphenylene oxide, polyphenylene sulfide, polyphthalamide, polystyrene, polysulfone, polytrimethylene terephthalate, polyurethane, polyvinyl acetate, polyvinyl chloride, polyvinylidene chloride, styrene-acrylonitrile, and combinations or copolymers thereof;
   providing a first metathesis catalyst; and
   reacting the first and second polymers in the presence of the metathesis catalyst under conditions sufficient to form a crosslinked polymer.

2. The method of claim 1, wherein the first metathesis catalyst is a ruthenium-based catalyst.

3. The method of claim 2, wherein the ruthenium-based catalyst is selected from the group consisting of: a Grubbs First Generation-type catalyst, a Grubbs Second Generation-type catalyst, and a combination thereof.

4. The method of claim 1, wherein the first metathesis catalyst has a catalyst concentration of between approximately 0.1 mol % and approximately 10 mol % catalyst per mol non-hindered olefin in the first and second thermoplastic polymers.

5. The method of claim 1, wherein the olefin content is between approximately 0.1% by weight and approximately 10% by weight.

6. The method of claim 1, wherein the reacting results in a crosslinking yield of between approximately 50% and approximately 80%.

7. The method of claim 1, wherein the reacting results in a crosslinking yield of at least approximately 70%.

8. The method of claim 1, wherein the reacting results in an improvement in tensile strength of a modulus at 100% elongation by at least approximately three times over crosslinking by electron beam radiation at 10 MRads.

9. The method of claim 1, wherein the crosslinked polymer may be decrosslinked by:
   providing ozone; and
   reacting the crosslinked polymer with the ozone under conditions sufficient to decrosslink the crosslinked polymer, forming a decrosslinked polymer having a pendant aldehyde.

* * * * *